US008882802B2

(12) United States Patent
Kao

(10) Patent No.: US 8,882,802 B2
(45) Date of Patent: Nov. 11, 2014

(54) CHIROPRACTIC MACHINE

(76) Inventor: Yi-Chin Kao, Taipei (TW)

( * ) Notice: Subject to any disclaimer, the term of this patent is extended or adjusted under 35 U.S.C. 154(b) by 323 days.

(21) Appl. No.: 13/241,120

(22) Filed: Sep. 22, 2011

(65) Prior Publication Data

US 2013/0079823 A1 Mar. 28, 2013

(51) Int. Cl.
*A61F 5/00* (2006.01)
*A61H 1/02* (2006.01)

(52) U.S. Cl.
CPC ............ *A61H 1/0292* (2013.01); *A61H 1/0222* (2013.01); *A61H 2201/1246* (2013.01); *A61H 2201/0142* (2013.01); *A61H 2201/1607* (2013.01)
USPC ........................................... 606/240; 603/237

(58) Field of Classification Search
USPC ........... 606/237, 240–245; 601/23, 24; 5/612, 5/616–618; 128/845; 482/142; 602/32–36
See application file for complete search history.

(56) References Cited

U.S. PATENT DOCUMENTS

2003/0055456 A1* 3/2003 Cox .............................. 606/243

* cited by examiner

*Primary Examiner* — Justine Yu
*Assistant Examiner* — Kathrynn Reilly
(74) *Attorney, Agent, or Firm* — Pro-Techtor Int'l Services; Ian Oglesby

(57) ABSTRACT

A chiropractic machine is disclosed which uses separate supporting members for the various body parts of a patient. These separate supporting members are mounted on a flexible structure that allows them to be rotated and elongated in relation to each other. This allows greater flexibility and range of motion, thus facilitating chiropractic treatment.

8 Claims, 17 Drawing Sheets

CHIROPRACTIC MACHINE

BACKGROUND OF THE INVENTION

1. Field of the Invention

The invention relates to a chiropractic machine, and more particularly, to a chiropractic machine employing the physiotherapy and lower back-part motion methods to be applied in cervical vertebrae and vertebral of human body so as to achieve the object of rehabilitation and treating the pain in vertebral.

2. Description of the Prior Art

Following the working pressure of workers of modern life and higher and higher tension of life style as well as the improper poise of carrying heavy weight, heavy working burden, insufficient motion for long time fixed poise in standing and sitting, and frequent repeated bending, people generates pains in their muscle or symptoms of pain and numb in their cervical vertebrae, thoracic vertebrae, and lumbar vertebrae etc., and in association, results in unwell in their visceral. Therefore, by the use of the rehabilitation method through the lower-back-part motion to perform redress and physiotherapy for their vertebral in a short time, their vertebral nerve can be soothed to relieve their pain and paralysis thoroughly.

In general, methods for treating cervical vertebrae and vertebral disease are no other than medicinal treatment, physical treatment, and surgical treatment. Surgical treatment can be employed for serious disease while muscular electric stimulation, protection belt, auxiliary medical equipment, or having a person performing massage rehabilitation can be helpful to improve the above-mentioned symptoms for trivial disease. There are two objects for performing physical treatment, that is, to improve the pain symptom and to slow down the degeneration process of cervical vertebrae and vertebral. However, the rehabilitation works of physical treatment are mostly undertaken by persons for performing rehabilitation. Nevertheless, the angle and the magnitude of the strength of exerting force are hard to control. Consequently, the user is unable to obtain complete rehabilitation. Moreover, most of the auxiliary medical equipments currently seen are designed for single function. They are slow in treatment, non-obvious in function, limited in treatment effect, besides, they are not necessary all adequate for the user, thereby, short of safety and practicality.

Therefore, just how to design a rehabilitation equipment to overcome the above-mentioned shortcomings becomes necessary in the industry.

SUMMARY OF THE INVENTION

In light of the above-mentioned disadvantages of the prior art, the invention provides a chiropractic machine to treat the pain and paralysis of the vertebral of the body for the user effectively, safely, and practically. It aims to ameliorate at least some of the disadvantages of the prior art or to provide a useful alternative.

The primary objective of the invention is to provide a chiropractic machine using the set-up of computer controlled program or manual controller and by the use of optimum input data to automatically execute the assistance work for the user, and simultaneously or individually adjust several parts of human body to cure the symptoms in accordance with the requirements of the user.

The secondary objective of the invention is to provide a multi-function lower back-part motion chiropractic machine to avoid the risk resulted from the improper machine design in order to help the user have a safe rehabilitation, and redress to achieve the improvement of the syndromes of the cervical vertebrae, and vertebral etc.

The other objective of the invention is to provide a multi-function lower back-part motion chiropractic machine to perform rehabilitation-and-physiotherapy by him/her self. Particularly, before the active treatment of surgery, the symptom can be gradually healed by employing the chiropractic machine of the invention to perform rehabilitation and physiotherapy. The healing can even be achieved such that the surgery can be canceled.

To achieve the above-mentioned objectives, a chiropractic machine including a base, a pelvic part section, an abdominal part section, a leg part section, a head part section, a cervical part traction section, and mattresses is provided. By the use of a sixth drive device, the head part section is capable of rotating with respect to a second pivotally-connected shaft and a third pivotally-connected shaft to move up-and-down to help the user's head part perform motion. By the use of a fifth drive device, the abdominal part section is capable of swinging left-and-right with respect to a third pivotally-connected part to help the user's waist part perform exercise. By the use of a third drive device, the pelvic part is capable of rotating with respect to a central sliding rod to twist for traction-and-release to help the user's waist part perform motion. By the use of an elevating post and a first drive device, the base is capable of pushing the whole assembly of the chiropractic machine up-and-down to help the user's lower back part perform motion. By the use of a second drive device, the pelvic part is capable of rotating with respect to a first pivotally-connected shaft to push the pelvic part up-and-down to help the user's pelvic part perform motion. By the use of a fourth drive device, the pelvic part is capable of moving back-and-forth along with an outer sliding rod sleeve tube to help the user's pelvic part doing tighten and relaxing motion. By the use of a seventh drive device, the traction rod is capable of rotating up-and-down with respect to an adjusting seat to help the user's cervical part perform motion. By the use of a swing device and the second drive device, the pelvic part is capable of rotating up-and-down with respect to a first pivotally-connected shaft to help the user's lumbar vertebrae perform motion.

The accomplishment of this and other objectives of the invention will become apparent from the following description and its accompanying drawings of which:

DETAILED DESCRIPTION OF THE PREFERRED EMBODIMENT

Figure 1:
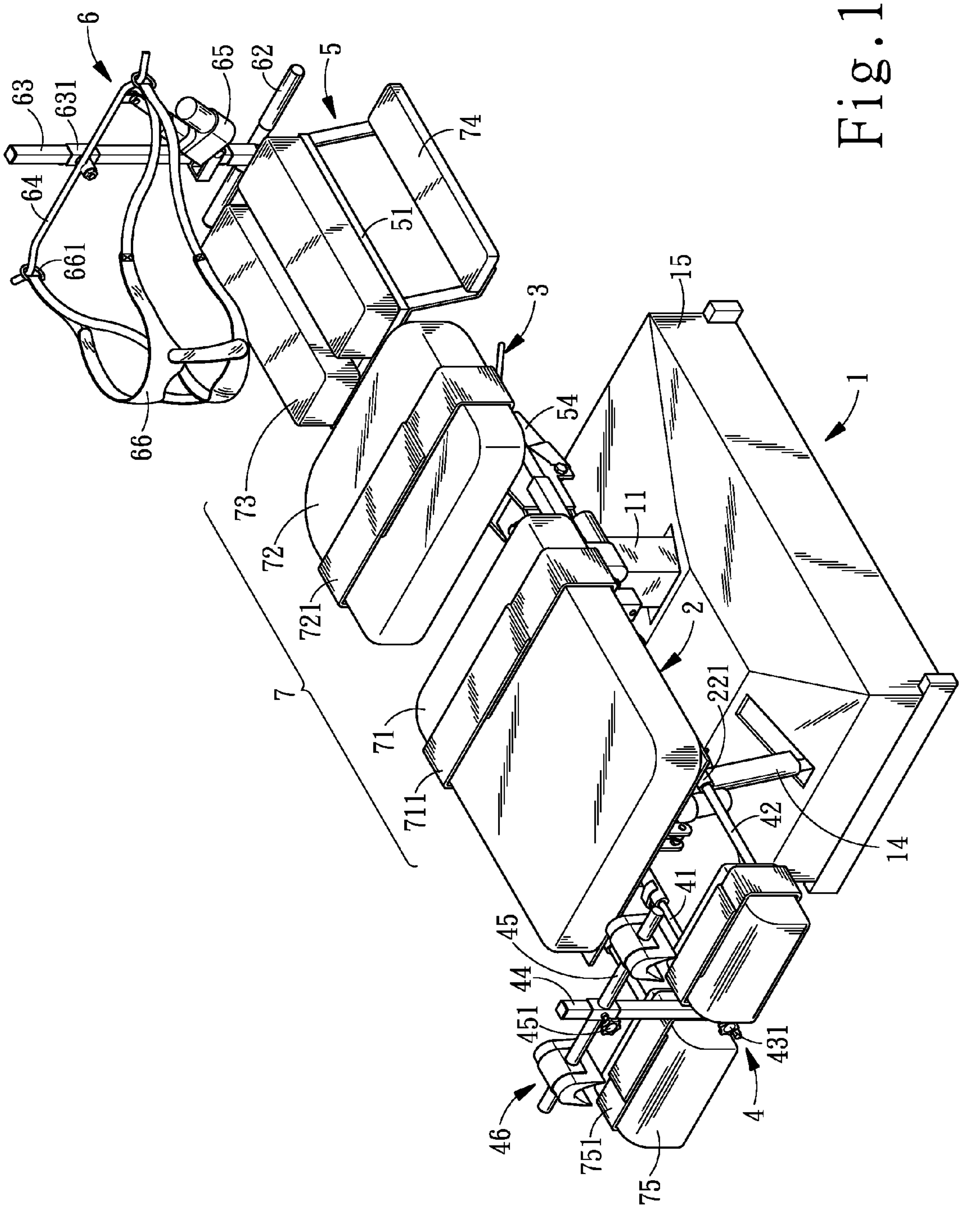
FIG. 1 is an isometric view of the chiropractic machine structure of the invention.
Figure 2:
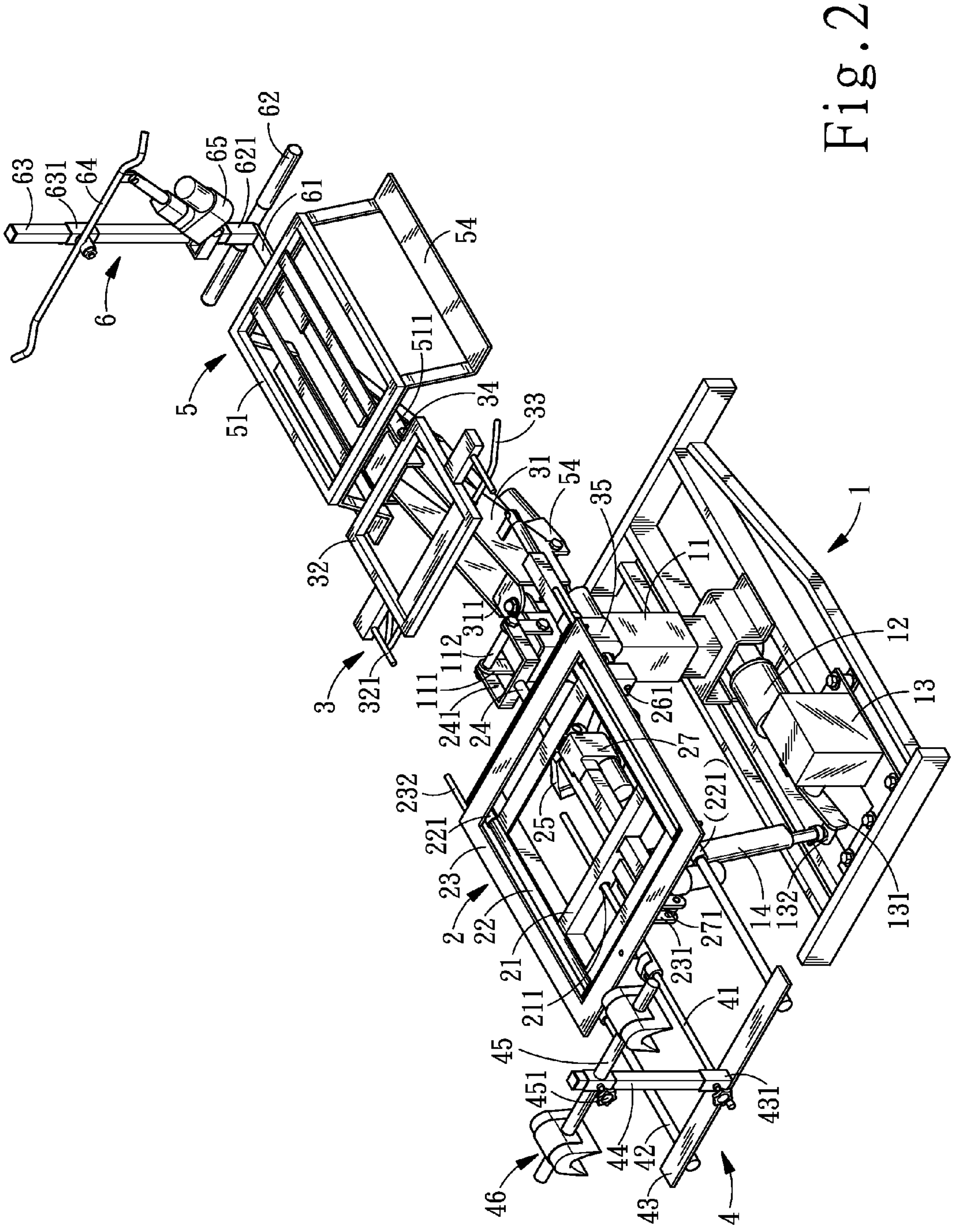
FIG. 2 is an isometric view of the mattress-removed chiropractic machine structure of the invention.

FIG. 1 is an isometric view of the chiropractic machine structure of the invention while FIG. 2 is an isometric view of the mattress-removed chiropractic machine structure of the invention. As shown in FIG. 1 and FIG. 2, the invention being set by a system program of the computer's central processing unit and executed by the optimum input data or being activated respectively or simultaneously by a plurality of manually controlled drive devices, mainly includes a base (1), a pelvic part section (2), an abdominal part section (3), a leg part section (4), a head part section (5), a cervical part traction section (6), and mattresses (7).

The base (1) includes an elevating post (11) at an appropriate location thereof, a first pivotally-connected part (111) at the end thereof, and a motion device (13), where the elevating post (11) has a first drive device (12) at an appropriate location thereof. The first drive device (12) can be driven by a motor, or a hydraulic cylinder, or a pneumatic cylinder. The motion device (13) also has a drive device (not shown in the FIG.) therein, and can be driven also by a motor, or a hydraulic cylinder, or a pneumatic cylinder. Moreover, the motion device (13) is connected to a second drive device (14) by a swing crank (131) through a swing shaft (132) and is secured at the bottom part of the pelvic part section (2) where the second drive device (14) can be driven also by a motor, or a hydraulic cylinder, or a pneumatic cylinder.

The pelvic part section (2) includes a pelvic part seat (21), an outer sliding rod (42) furnished on each side of the pelvic part seat (21), an outer sliding rod sleeve tube (22) also furnished on each side of the pelvic part seat (21), a central sliding rod (24), an adjusting rod (41), a sliding bracing frame (23), a rotating handle (25), a third drive device (26), and a fourth drive device (27).

Figure 2A:
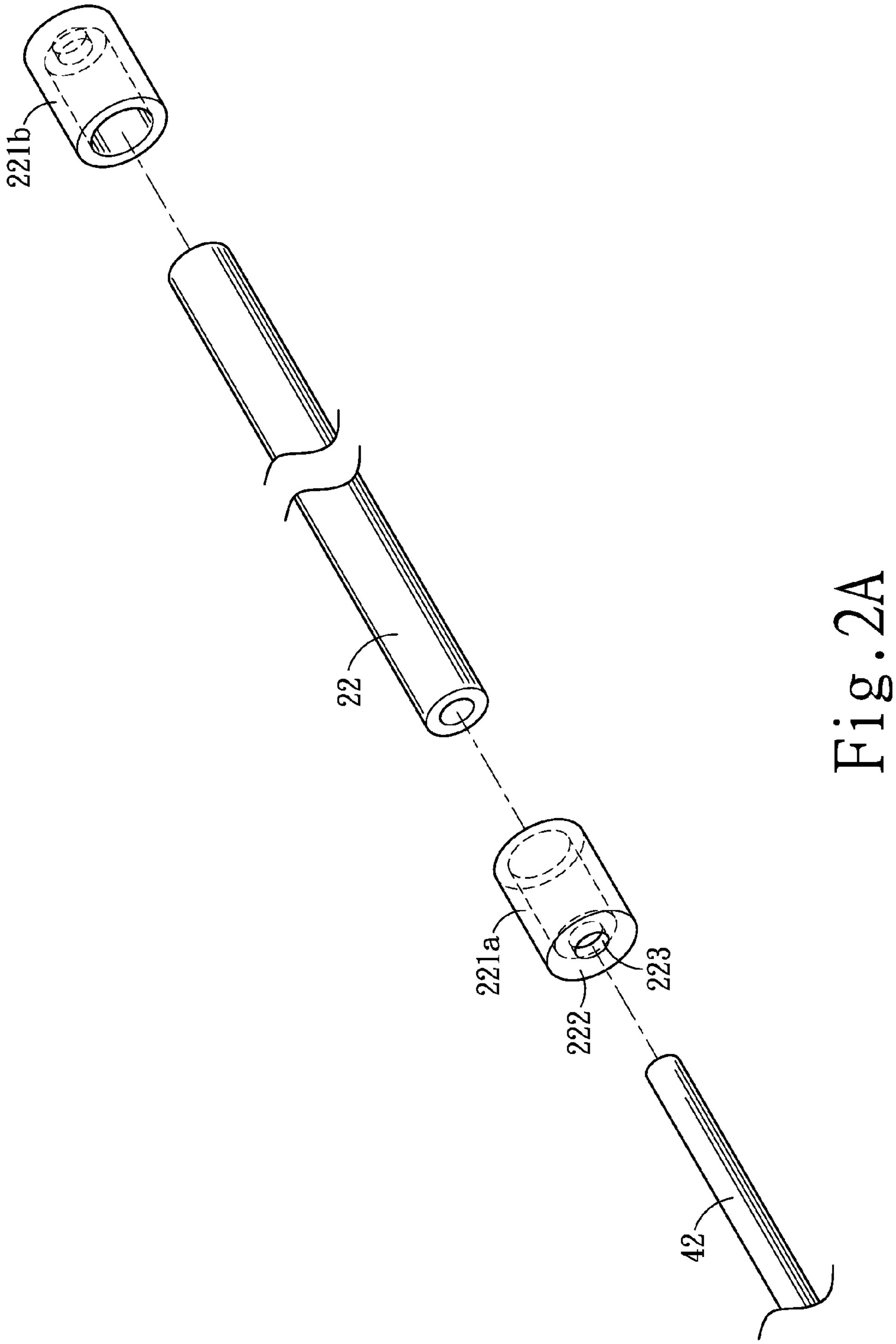
FIG. 2*a* is an isometric view of the outer sliding rod of the invention.
Figure 2B:
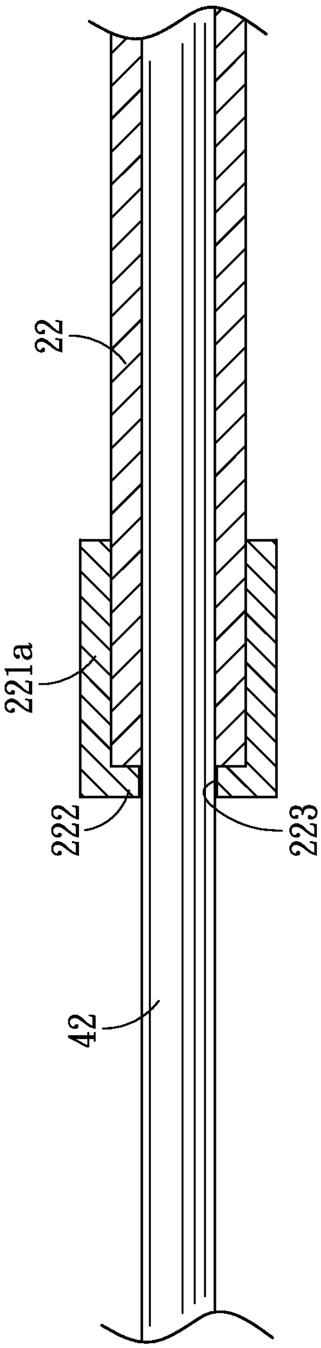
FIG. 2*b* is a longitudinal cross-sectional view of the outer sliding rod of the invention.

FIG. 2*a* is an isometric view of the outer sliding rod of the invention while FIG. 2*b* is a longitudinal cross-sectional view of the outer sliding rod of the invention. As shown in FIG. 2*a* and FIG. 2*b*, each of the outer sliding rod (42) and the outer sliding rod sleeve tube (22) has bearing sleeve tubes (221) where the beating sleeve tubes (221) further has an end wall (222) with a penetrating hole (223) provided thereat. Bee-Bearing sleeve tubes (221) are secured to the sliding bracing frame (23). The outer sliding rod sleeve tube (22) is disposed by penetrating each end in the beating sleeve tube (221). The outer sliding rod (42) on each side of the chiropractic machine is penetrated through the penetration hole (223) at the end wall (222), the beating sleeve tubes (221), and the outer sliding rod sleeve tube (22), successively, thereby, the outer sliding rod (42) is capable of sliding back-and-forth among them.

The central sliding rod (24) having its one end be furnished a second pivotally-connected part (241) is connected to the first pivotally-connected part (111) through a first pivotally-connected shaft (112). Both ends of the pelvic part seat (21) are connected to the outer sliding rod sleeve tubes (22) on both sides of the chiropractic machine. The central sliding rod (24) has a rotating handle (25) which has the third drive device (26) that is perpendicular to the central sliding rod (24). The third drive device (26) can be driven also by a motor, or a hydraulic cylinder, or a pneumatic cylinder. Moreover, one end of the third drive device (26) having a securing part (261) furnished at an end thereof is secured at a side below the pelvic part seat (21). What is more, a fourth drive device (27) capable of being driven also by a motor, or a hydraulic cylinder, or a pneumatic cylinder has a through hole (211) at the middle section of the pelvic part seat (21) for the fourth drive device (27) to penetrate through making the fourth drive device (27) parallel to the central sliding rod (24). Furthermore, at one end of the fourth drive device (27), an inserting peg (271) is furnished to be connected to a lug (231) provided beneath the sliding bracing frame (23) making it to be positioned above the pelvic part seat (21). In addition, a tightening band buckle peg (232) is provided at the sliding bracing frame (23) on each side of the chiropractic machine.

The abdominal part section (3) includes a bracing seat (31), an abdominal part seat (32), a slide-down rod (33), a second pivotally-connected shaft (34), and a fifth drive device (35). The bracing seat (31) has a third pivotally-connected part (311) furnished at one end which is connected to the elevating post (11) and the second pivotally-connected shaft (34) furnished at the other end. The fifth drive device (35), being furnished on a side of both the elevating post (11) and bracing seat (31) and can be driven also by a motor, or a hydraulic cylinder, or a pneumatic cylinder, has its one end connected to the elevating post (11) and its other end connected to the bracing seat (31).

The leg part section (4) includes an adjusting rod (41), the outer sliding rod (42), a leg part seat (43), an ankle supporting rod (44), an ankle securing brace (45) and ankle supports (46). The leg part seat (43) has a penetrating hole (211) provided at an appropriate location thereof to be penetrated for the adjusting rod (41) making the adjusting rod (41) to be parallel to the central sliding rod (24). A pair of ankle supports (46) attached on each side of the ankle securing braces (45) is provided. The ankle securing brace (45) is again supported at the center thereof by the ankle supporting rod (44) which has an adjusting part (451) for adjusting the elevation of the ankle securing brace (45) and the ankle supports (46). The ankle supporting rod (44) is secured and supported on the leg part seat (43) at the center thereof which is supported at an end of each of the parallel outer sliding rod (42) and the adjusting rod (41).

Figure 3:
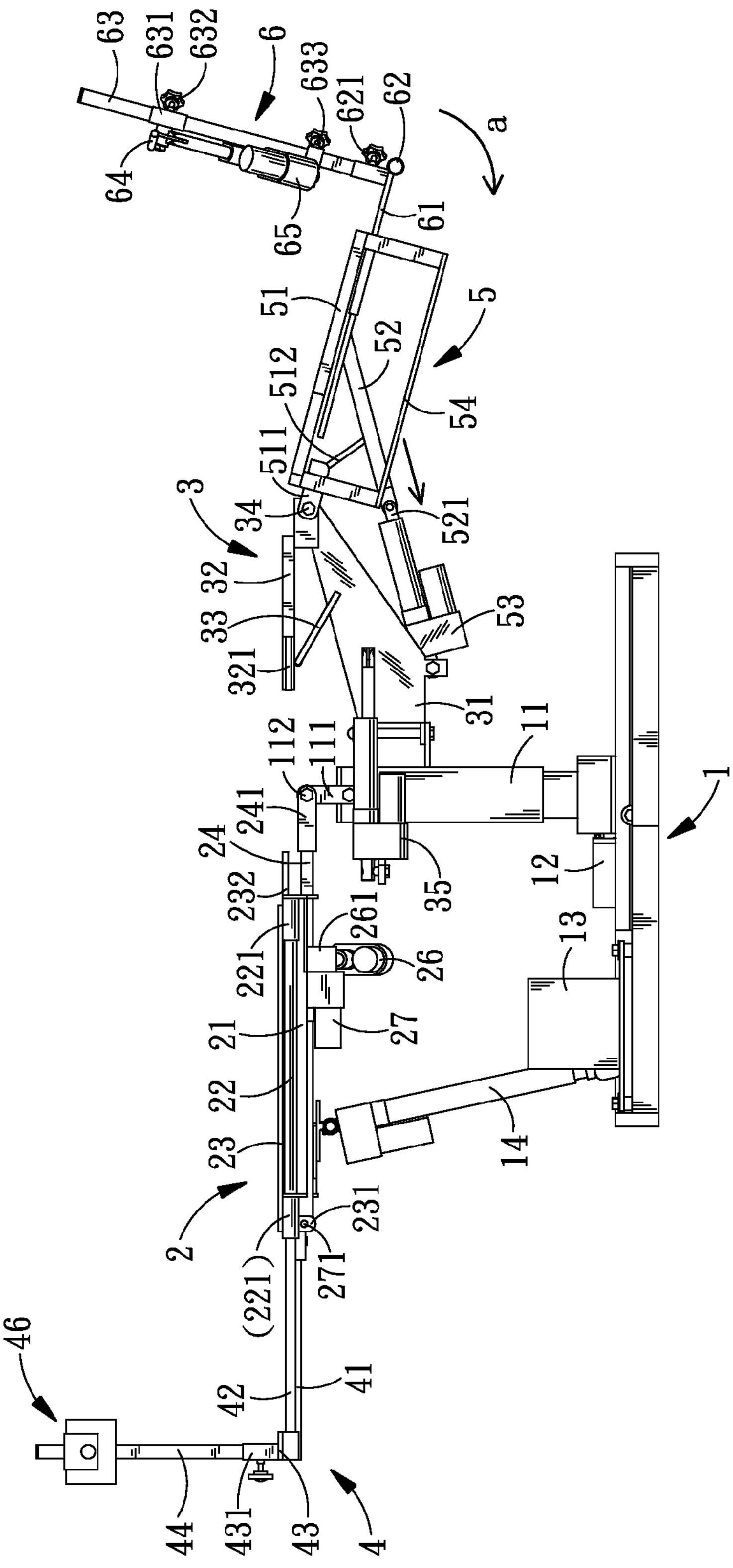
FIG. 3 is a front view of the head part section of the chiropractic machine of the invention showing the downward action.
Figure 4:
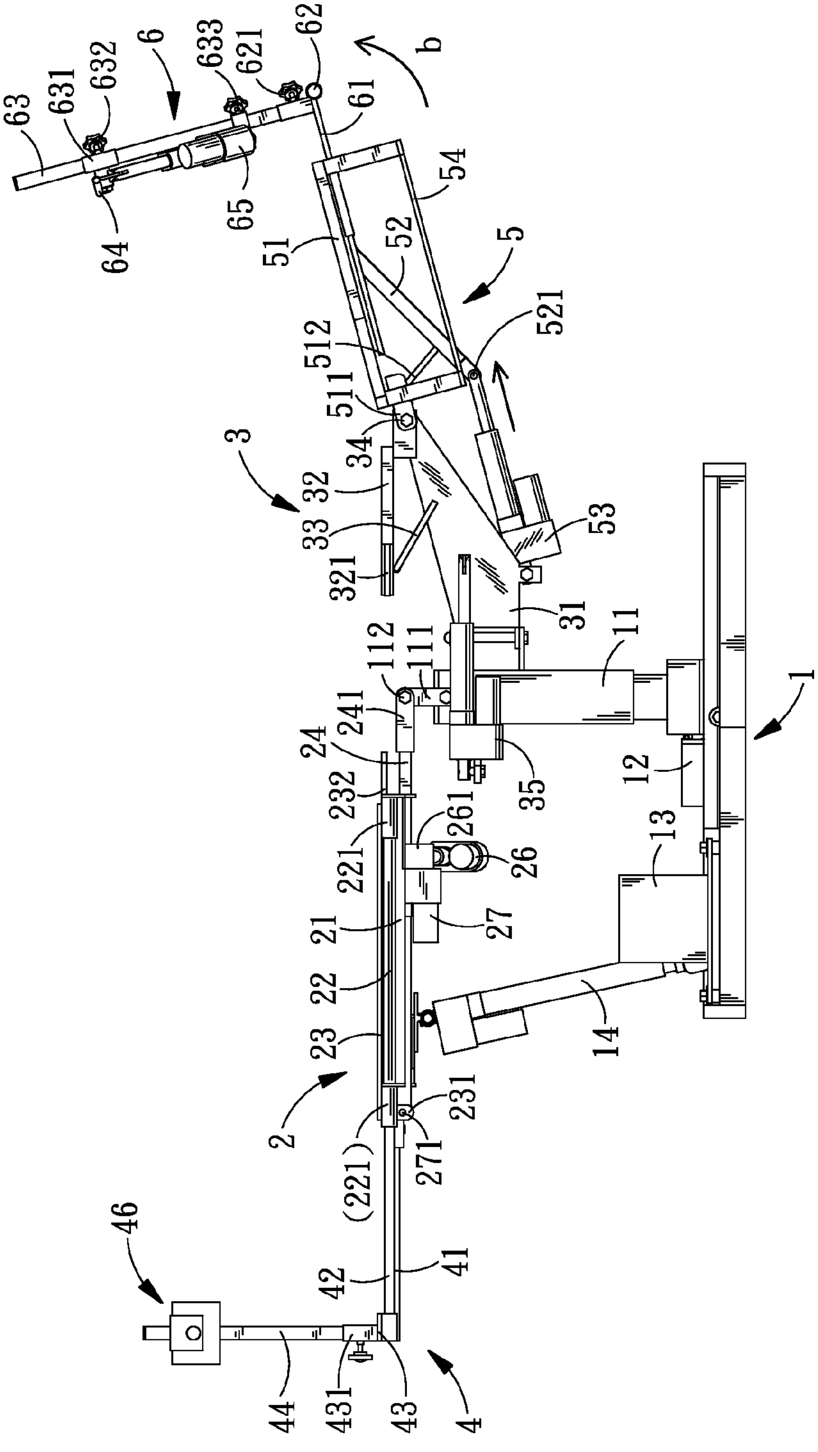
FIG. 4 is a front view of the head part section of the chiropractic machine of the invention showing the upward action.

FIG. 3 is a front view of the head part section of the chiropractic machine of the invention showing the downward action while FIG. 4 is a front view of the head part section of the chiropractic machine of the invention showing the upward action. As shown in FIG. 1, FIG. 2, FIG. 3, and FIG. 4, the head part section (5) includes a head pillow rack (51), a first supporting rod (52), a sixth drive device (53), and a handle seat (54). The head pillow rack (51) has a securing part (511) furnished to be connected to the second pivotally-connected shaft (34) furnished on the bracing seat (31) of the abdominal part section (3). The first supporting rod (52) has a third pivotally-connected shaft (521) furnished to be connected to the sixth drive device (53) which is further connected to the bottom of the bracing seat (31). The sixth drive device (53) can be driven also by a motor, or a hydraulic cylinder, or a pneumatic cylinder. The securing part (511) has a slant supporting rod (512) furnished with its one end connected to the securing part (511) while with its other end connected to the appropriate location in the mid-section of the first supporting rod (52). Moreover, the handle seats (54) are furnished on each side of the head pillow rack (51).

The cervical part traction section (6) includes an adjusting rod (61), a handle rod (62), a second supporting rod (63), a traction rod (64), a seventh drive device (65), and a cervical part traction band (66). The second supporting rod (63) having an adjusting seat (631) slipping thereon is attached to the handle rod (62) at the center thereof and then connected to the adjusting rod (61). The adjusting seat (631) has the traction rod (64) and an upper adjusting seat securing part (632) furnished thereon. The seventh drive device (65) has its one end attached to the traction rod (64) at a side and has its other end secured to the second supporting rod (63) with a upper adjusting seat securing part (632) furnished thereat. By the use of a retaining ring (661), the cervical part traction band (66) is secured to the traction rod (64).

The mattress (7) includes a plurality of mattress bodies (71), (72), (731), (74), and (75). The mattress bodies (71), (72), and (75) are tightened by a tightening band (711), (721), and (751) respectively.

When it comes to assembling, the elevating post (11), furnished by the base (1), has one end of its first pivotally-connected part (111) employ the first pivotally-connected shaft (112) to connect to the second pivotally-connected part (241) furnished by one side of the pelvic part (2), and has its other end connect to the bracing seat (31) of the abdominal part section (3), then the abdominal part seat (32) is installed above it. On the other side of the butt part (2), the outer sliding rod (42) of the leg part section (4) is slipped in the outer sliding rod sleeve tube (22). The second pivotally-connected shaft (34) furnished at the other end of the bracing seat (31) is connected to the securing part (511) furnished on a side of the head part section (5). The other side of the head part section (5) is connected to the adjusting rod (61) of the cervical part traction section (6). The mattress body (71) of the mattress (7) is placed on the pelvic part (2) and is tightened by the tightening band (711) tightening around the tightening band buckle peg (232). Similarly, the mattress body (72) is placed on the abdominal part section (3) and is tightened by the tightening band (721) tightening around the tightening band buckle peg (321). Subsequently, the mattress body (73) is installed in the head part section (5), the mattress body (74) is installed on the handle (54) of the head part section (5), and the mattress body (75) is installed in leg part section (4) with a tightening band (751). Finally, a housing (15) (not shown in the FIG.) is capped on the base (1).

FIG. 3 through FIG. 15 shows the usage of the chiropractic machine of the invention.

FIG. 3 is a front view of the head part section of the chiropractic machine of the invention showing the downward action while FIG. 4 is a front view of the head part section of the chiropractic machine of the invention showing the upward action. As shown in FIG. 3, and FIG. 4, one end of the first supporting rod (52), furnished beneath the head pillow rack (51), is pivotally connected to the sixth drive device (53) by the third pivotally-connected shaft (521) while the head part section (5) and the abdominal part section (3) are pivotally connected by the second pivotally-connected shaft (34). As shown in FIG. 3, once the sixth drive device (53) starts the telescoping action, the head part section (5) is capable of performing downward motion as it rotates with respect to the second pivotally-connected shaft (34) and the third pivotally-connected shaft (521) following in a first direction (a) when the sixth drive device (53) performs retracting action. Similarly, as shown in FIG. 4, the head part section (5) is capable of performing upward motion as it rotates with respect to the second pivotally-connected shaft (34) and the third pivotally-connected shaft (521) following in a second direction (b) when the sixth drive device (53) performs extending action. In this way, the user is capable of employing the head part section (5) of the chiropractic machine of the invention to perform his/her pelvic-part-motion.

Figure 5:
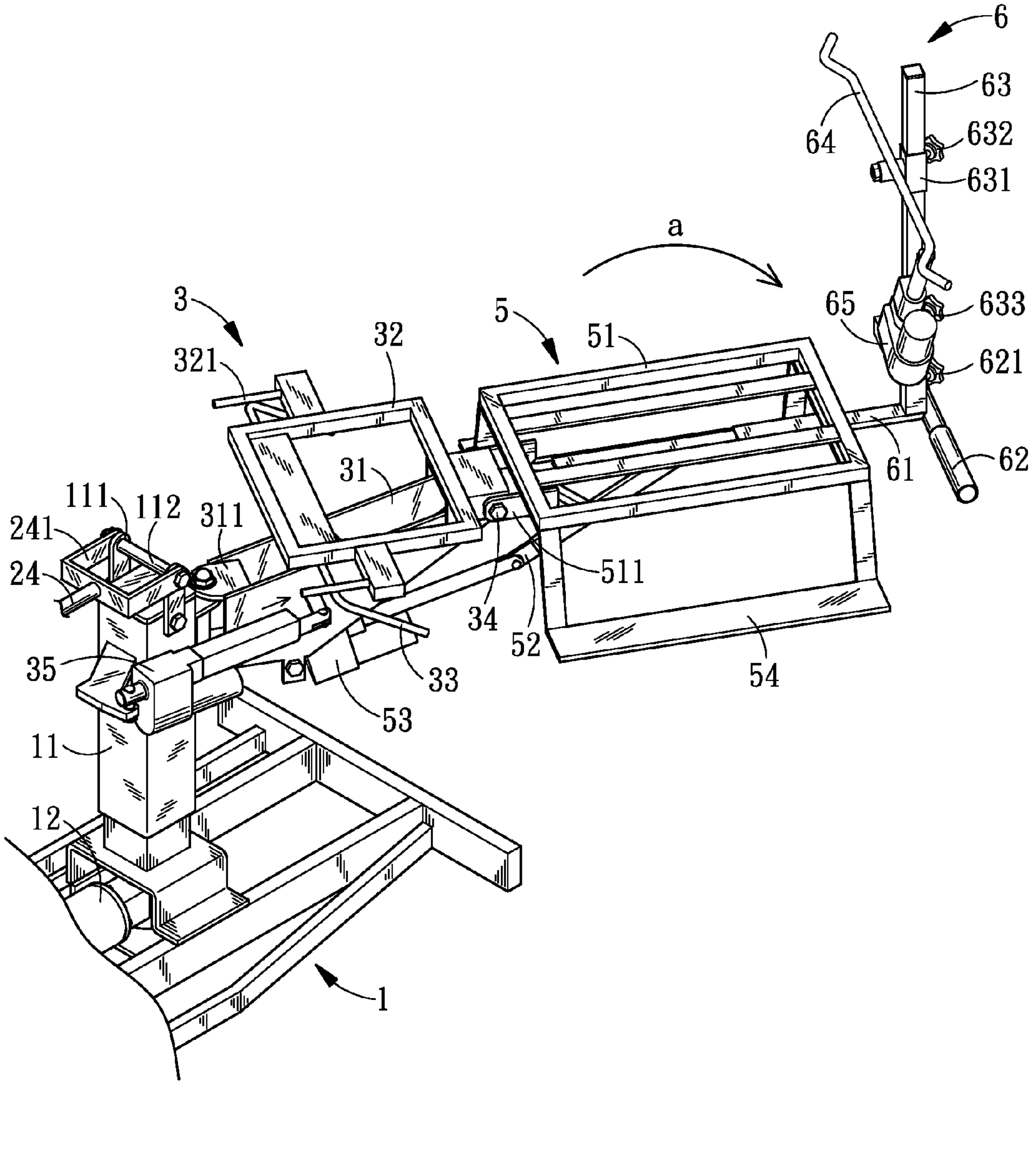
FIG. 5 is a schematic isometric view (I) the abdominal part section of the chiropractic machine structure of the invention showing the motion action.
Figure 6:
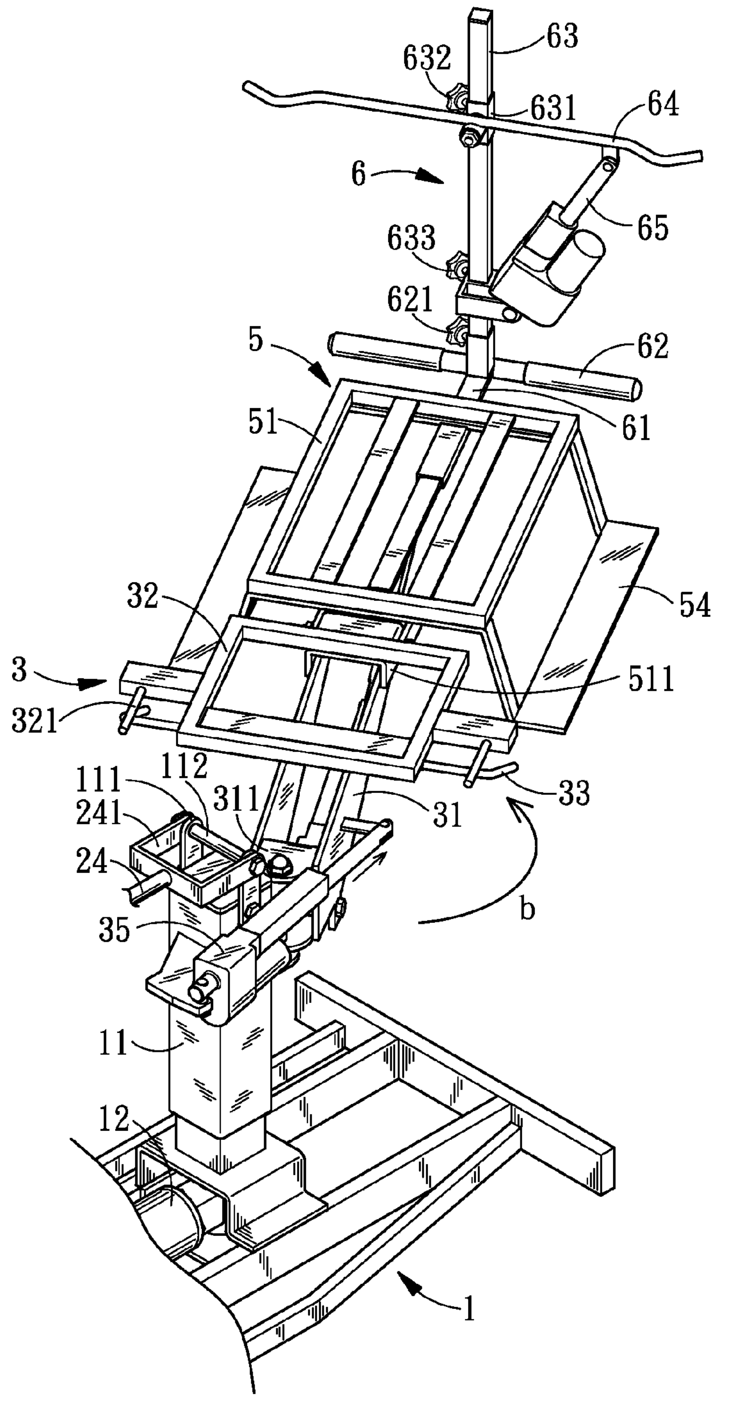
FIG. 6 is a schematic isometric view (II) the abdominal part section of the chiropractic machine structure of the invention showing the motion action.

FIG. 5 is a schematic isometric view (I) the abdominal part section of the chiropractic machine structure of the invention showing the motion action while FIG. 6 is a schematic isometric view (II) the abdominal part section of the chiropractic machine structure of the invention showing the motion action. As shown in FIG. 5 and FIG. 6, the abdominal part section (3) is connected to the elevating post (11) through the third pivotally-connected part (311). Moreover, the fifth drive device (35) of the abdominal part section (3) has its one end connect to the elevating post (11) and has its other end connect to the bracing seat (31). Since the fifth drive device (35) is furnished on one side of the abdominal part section (3), when the telescoping action of the fifth drive device (35) is in the middle of the stroke, the adjusting rod (61) connected to the head part section (5) is collinear with the central sliding rod (24) of the pelvic part section (2). Once the fifth drive device (35) starts the telescoping action, as shown in FIG. 5, the abdominal part section (3) will rotate in the first direction (a) with respect to the third pivotally-connected part (311) when the fifth drive device (35) performs retracting action. Similarly, as shown in FIG. 6, the abdominal part section (3) will rotate in the second direction (b) with respect to third pivotally-connected part (311) when the fifth drive device (35) performs extending action. In this way, the user is capable of employing the abdominal part section (3) of the chiropractic machine of the invention to perform his/her waist-part-motion to swing to the left-and-right hand sides in both the first direction (a) and the second direction (b).

Figure 7:
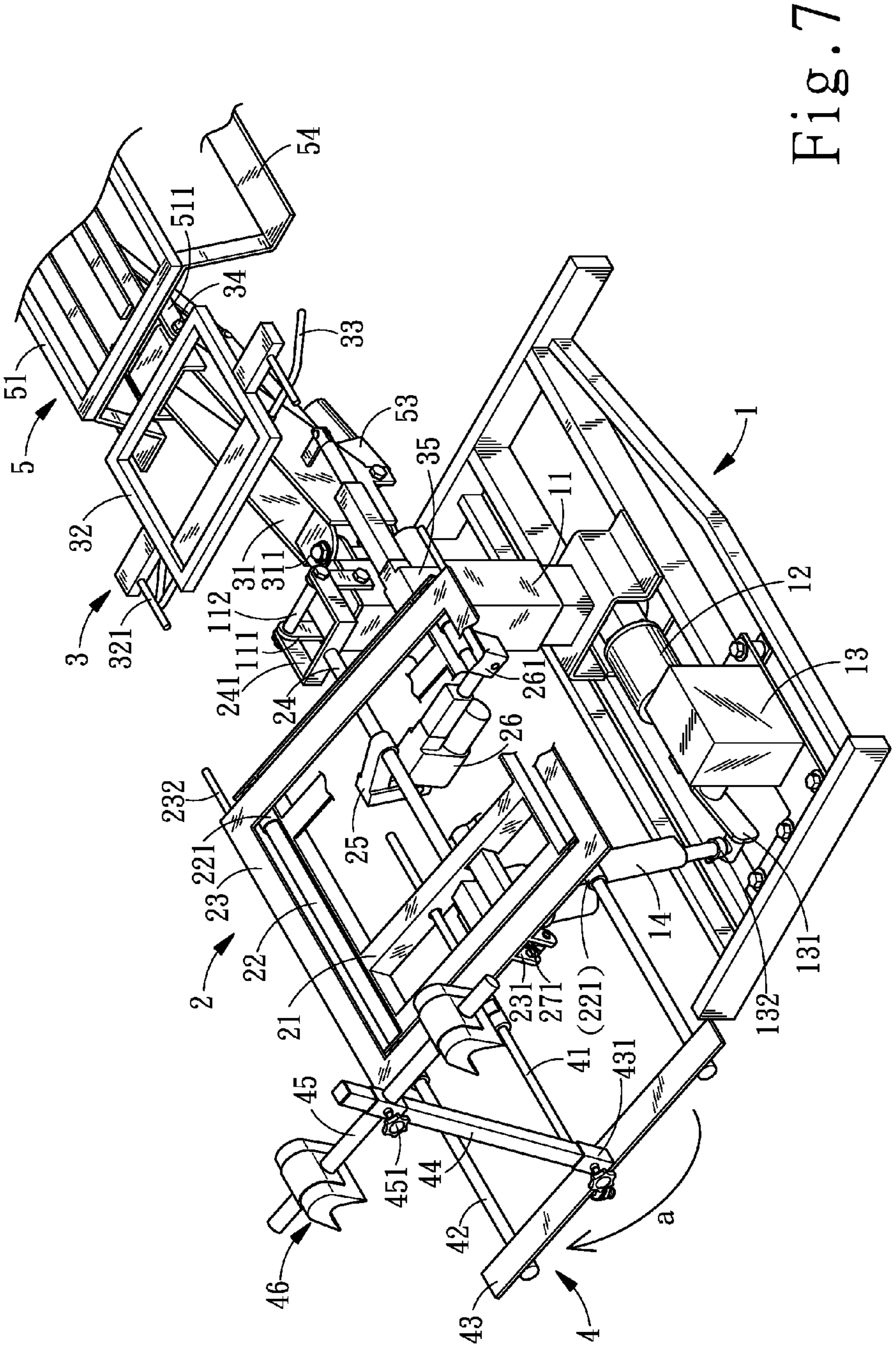
FIG. 7 is a schematic isometric view (I) the pelvic part section of the chiropractic machine structure of the invention showing the rotating action.
Figure 8:
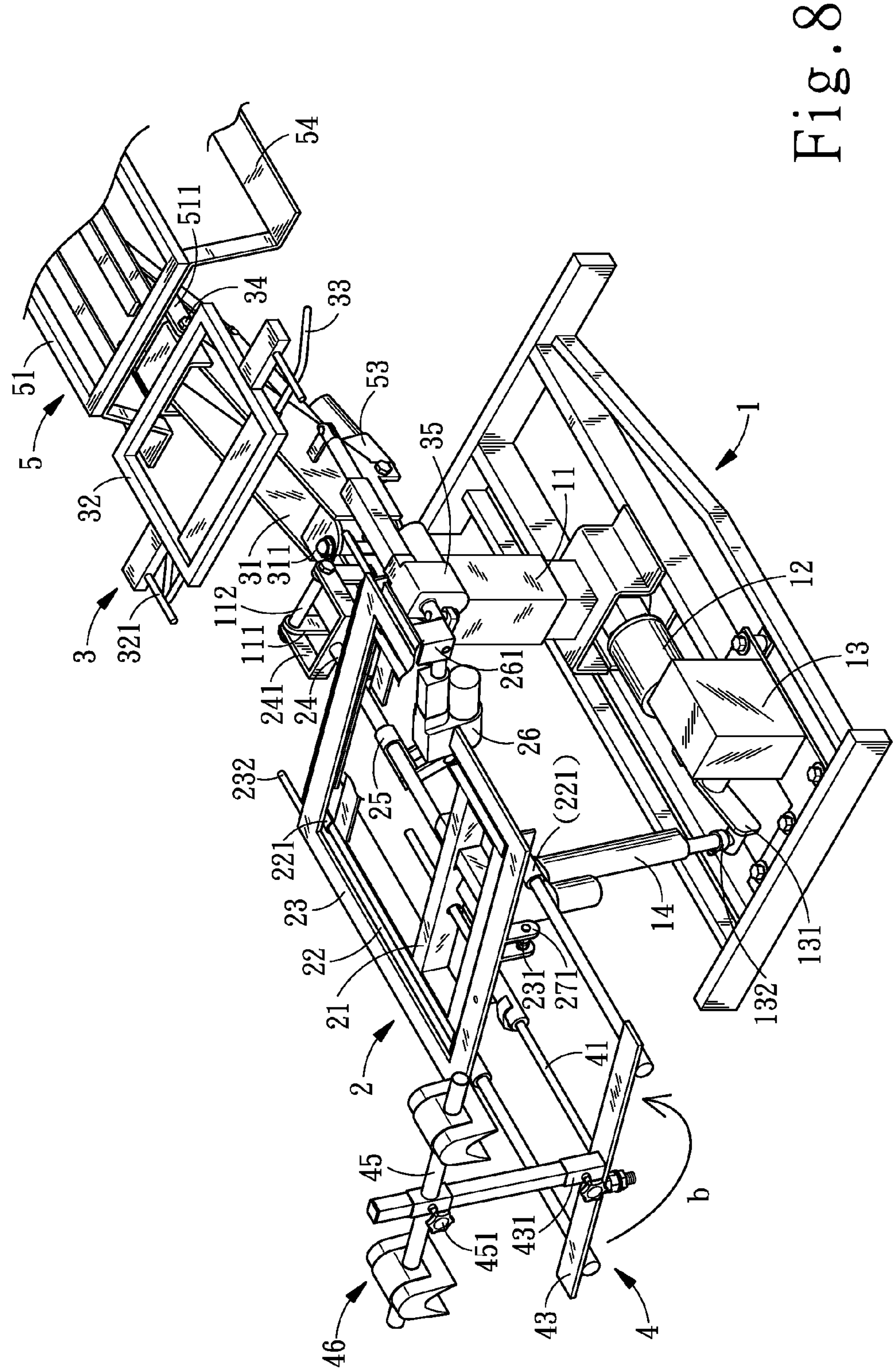
FIG. 8 is a schematic isometric view (II) the pelvic part section of the chiropractic machine structure of the invention showing the rotating action.

FIG. 7 is a schematic isometric view (I) the pelvic part section of the chiropractic machine structure of the invention showing the rotating action while FIG. 8 is a schematic isometric view (II) the pelvic part section of the chiropractic machine structure of the invention showing the rotating action. As shown in FIG. 1 and FIG. 8, the first pivotally-connected part (111) of the central sliding rod (24) is pivotally connected to the second pivotally-connected part (241) of the base (1). Since the rotating handle (25) of the third drive device (26) is furnished at an appropriate location of the central sliding rod (24), and the third drive device (26) has its one end connect to a side below the pelvic part seat (21) by the securing part (261), when the third drive device (26) is in the middle of the stroke, the pelvic part section (2) is horizontal position. Once the third drive device (26) starts the telescoping action, as shown in FIG. 7, the pelvic part section (2) will rotate in the first direction (a) with respect to the central sliding rod (24) by the use of the rotating handle (25) when the third drive device (26) performs retracting action. Similarly, as shown in FIG. 8, the butt part section (2) will rotate in the second direction (b) with respect to the central sliding rod (24) by the use of the rotating handle (25) when the third drive device (26) performs extending action. In this way, the user is capable of employing the pelvic part section (2) together with the leg part section (4) of the chiropractic machine of the invention to perform his/her waist-part-motion to twist in the first direction (a) and the second direction (b).

Figure 9:
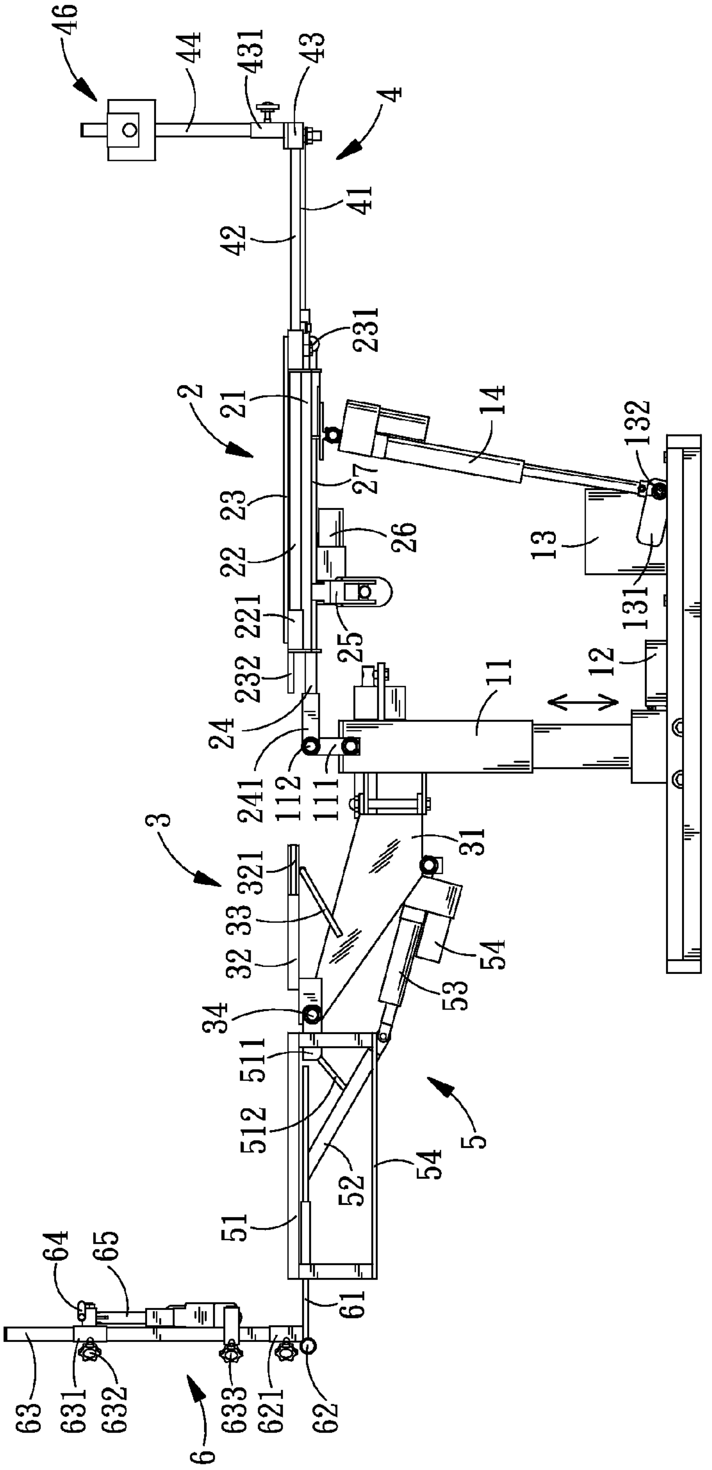
FIG. 9 is a schematic front view of the chiropractic machine structure of the invention showing the overall uplift variable height.

FIG. 9 is a schematic front view of the chiropractic machine structure of the invention showing the overall elevation adjustment. As shown in FIG. 9, as the elevating post (11) furnished by the base (1) starts to perform retracting action through first drive device (12), the elevating post (11) is capable of carrying the whole upper assembly of members to descend. Similarly, as the elevating post (11) starts to perform extending action through first drive device (12), the elevating post (11) is capable of carrying the whole upper assembly of members to ascend. In this way, the chiropractic machine of the invention is capable of adjusting the elevation of the multi-function lower back-part motion apparatus in accordance with the requirements of the user.

Figure 10:
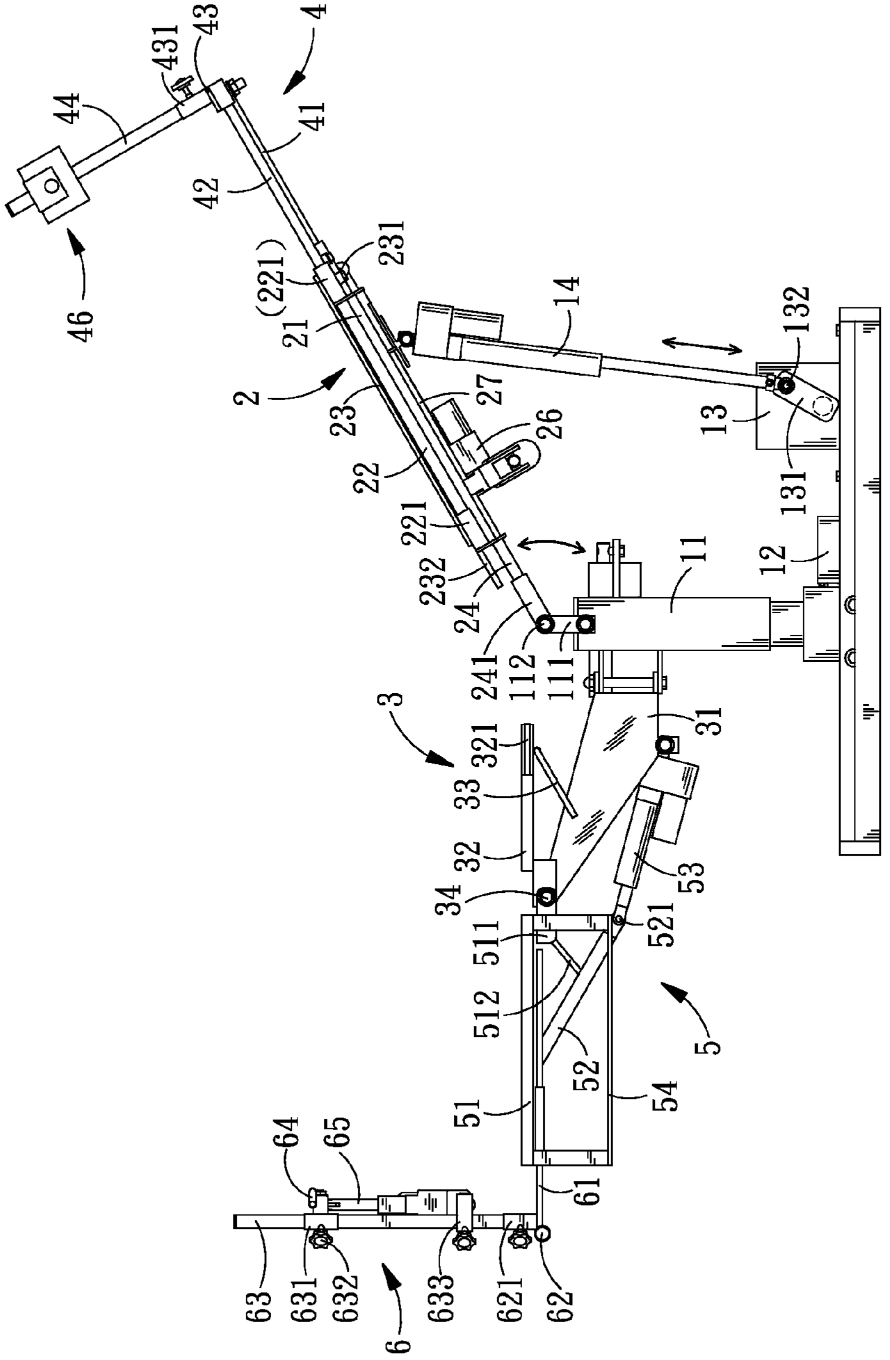
FIG. 10 is a schematic front view of the pelvic part section of the chiropractic machine structure of the invention showing the angle ascending-and-descending action.

FIG. 10 is a schematic front view of the pelvic part section of the chiropractic machine structure of the invention showing the ascending-and-descending action. As shown in FIG. 10, the motion crank (131) of the motion device (13) furnished at an appropriate location on the base (1) is pivotally connected to the second drive device (14) by the motion shaft (132) where one end thereat is secured at the bottom of the pelvic part section (2). When it comes to telescoping action of the second drive device (14), the pelvic part section (2) is capable of rotating with respect to the first pivotally-connected shaft (112) to move downward when the second drive device (14) performs retracting action. Similarly, the pelvic part section (2) is capable of rotating with respect to the first pivotally-connected shaft (112) to move upward when the second drive device (14) performs extending action. In this way, the user is capable of using the chiropractic machine of the invention to adjust the up-and-down motion angle of the pelvic part section (2) to change the up-and-down angle of the pelvic part in accordance with his/her requirement.

Figure 11:
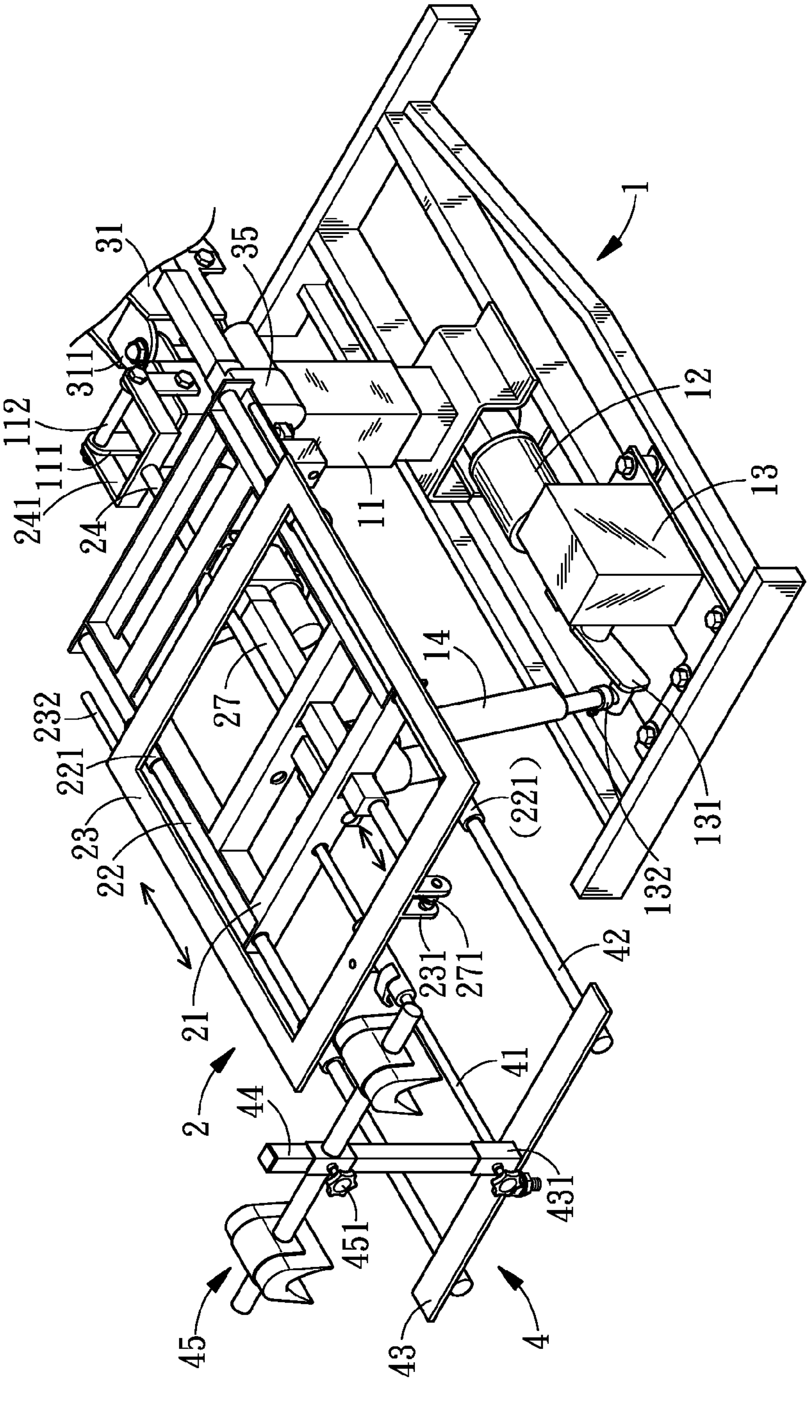
FIG. 11 is a schematic isometric view of the pelvic section of the chiropractic machine of the invention showing the traction-and-release action.

FIG. 11 is a schematic isometric view of the pelvic section of the chiropractic machine of the invention showing the traction-and-release action. As shown in FIG. 11, the pelvic part section (2) has the fourth drive device (27), which is furnished in parallel to the central sliding rod (24), is connected to the lug (231) of the sliding bracing frame (23) through an inserting peg (271). Therefore, when the fourth drive device (27) starts to perform telescoping action, the sliding bracing frame (23) is capable of performing traction-and-release movement along the outer sliding rod sleeve tube (22) to help the user having his/her pelvic perform relax and tightening motion.

Figure 12:
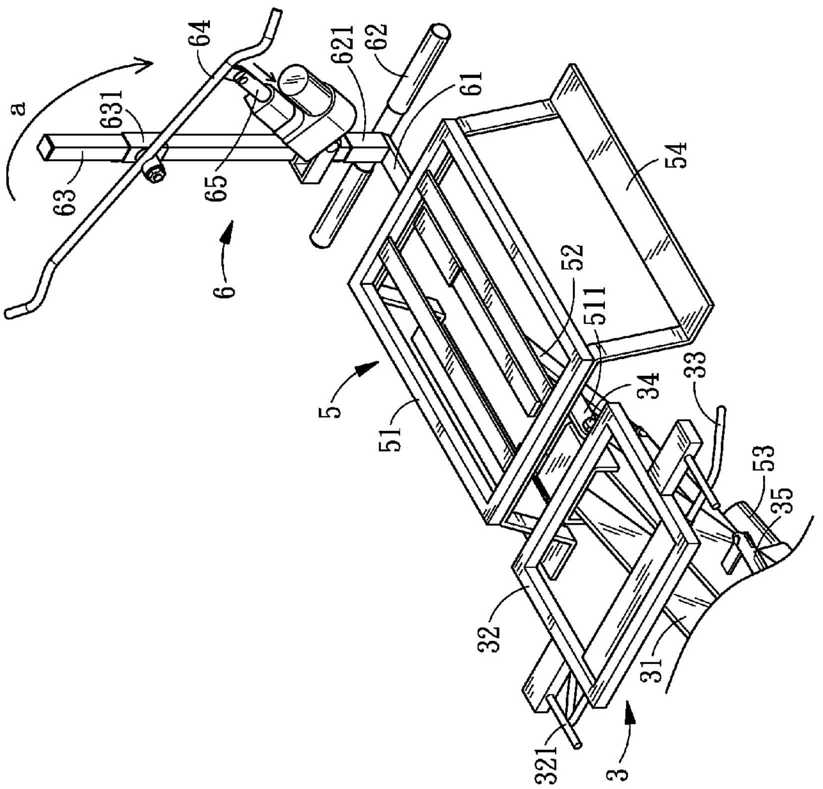
FIG. 12 is a schematic isometric view (I) of the cervical part traction rack of the chiropractic machine of the invention showing the rotating action.
Figure 13:
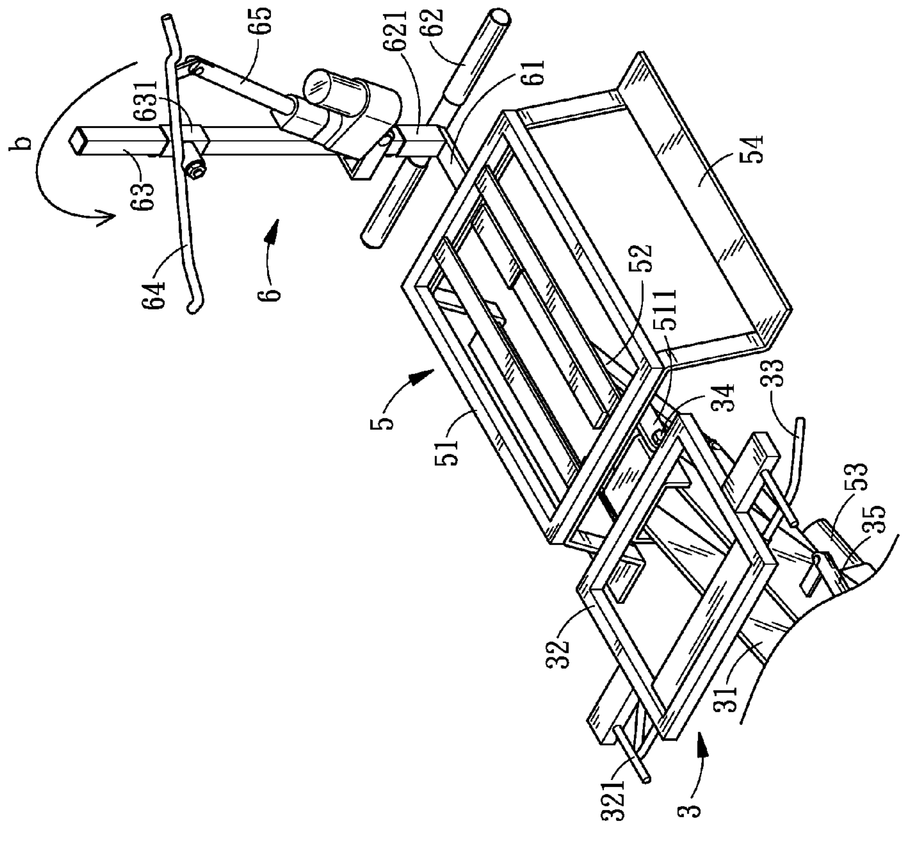
FIG. 13 is a schematic isometric view (II) of the cervical part traction rack of the chiropractic machine of the invention showing the rotating action.

FIG. 12 is a schematic isometric view (I) of the cervical part traction rack of the chiropractic machine of the invention showing the rotating action while FIG. 13 is a schematic isometric view (II) of the cervical part traction rack of the chiropractic machine of the invention showing the rotating action. As shown in FIG. 12 and FIG. 13, an end of the seventh drive device (65) is furnished and attached at the bottom of the second supporting rod (63) of the cervical part traction section (6) while the other end is attached to a side of the traction rod (64). The traction rod (64) is in horizontal position when the seventh drive device (65) is in the middle of the stroke. As shown in FIG. 12, as the seventh drive device (65) performs retracting action, the traction rod (64) will rotate in the first direction (a) with respect to adjusting seat (631) while as shown in FIG. 13, when the seventh drive device (65) performs extending action, the traction rod (64) will rotate in the second direction (b) with respect to adjusting seat (631). In this way, the cervical part traction section (6) of the chiropractic machine of the invention is capable of helping the user to perform rotation exercise of his/her cervical part.

Figure 14:
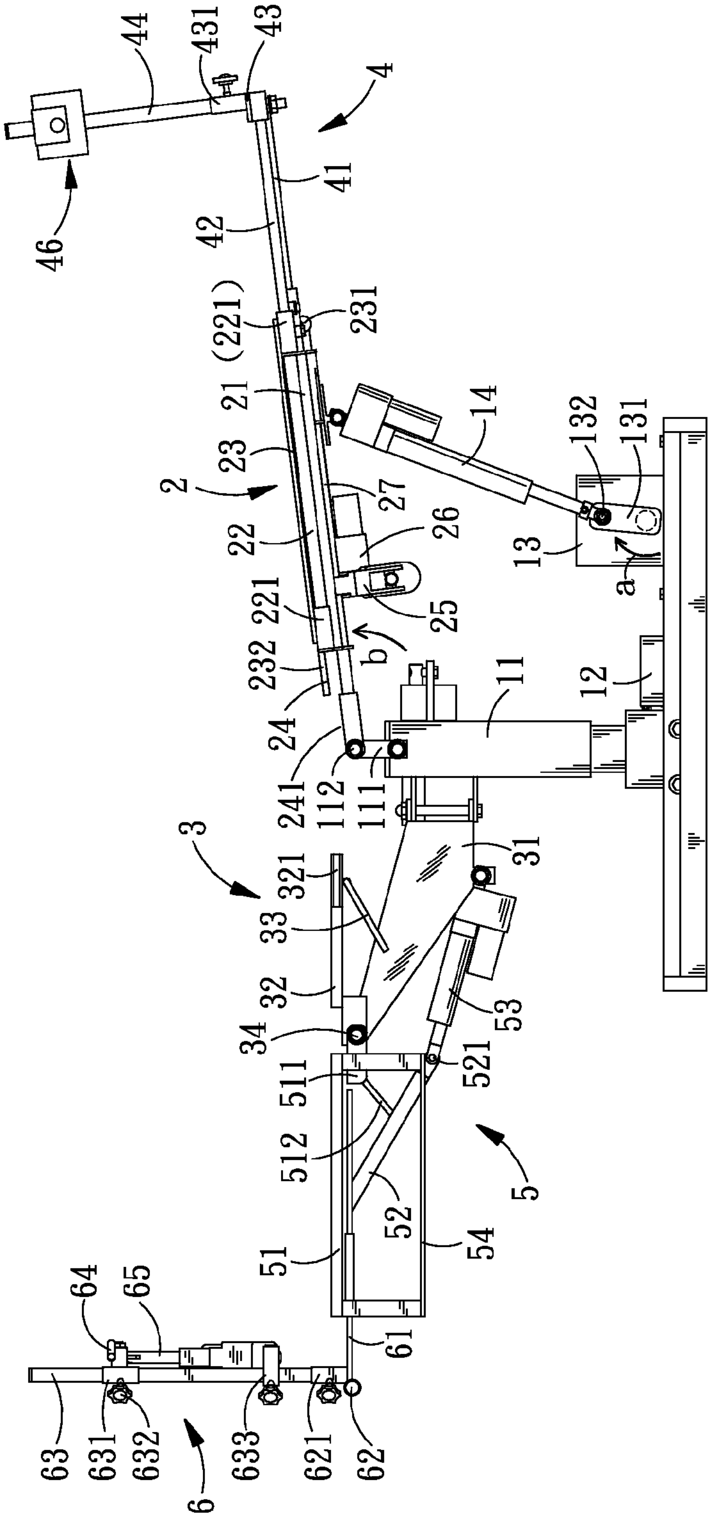
FIG. 14 is a schematic front view (I) of the pelvic part section of the chiropractic machine of the invention showing the flexion action.
Figure 15:
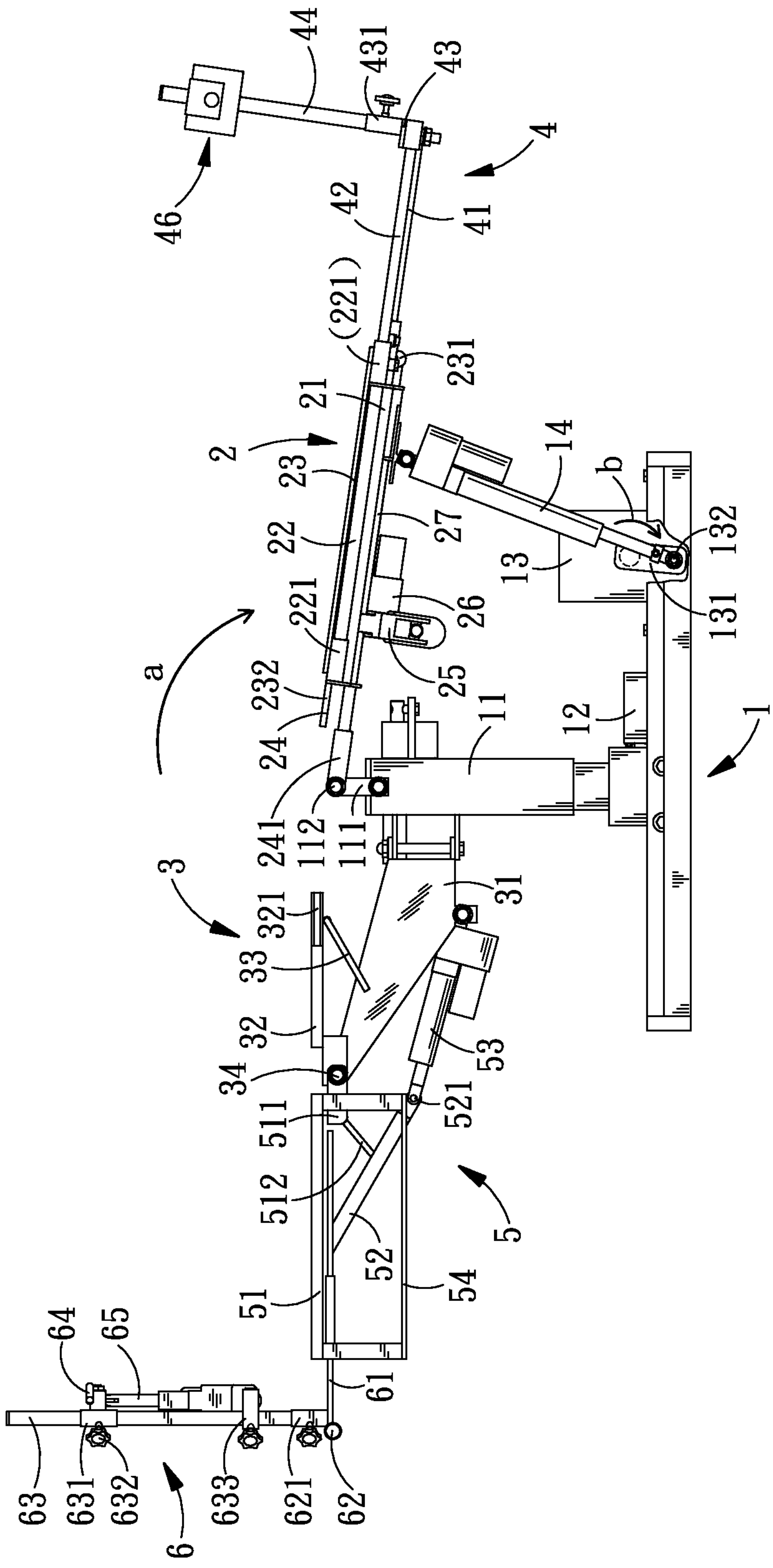
FIG. 15 is a schematic front view (II) of the pelvic part section of the chiropractic machine of the invention showing the flexion action.

FIG. 14 is a schematic front view (I) of the pelvic part section of the chiropractic machine of the invention showing the motion action while FIG. 15 is a schematic front view (II) of the pelvic part section of the chiropractic machine of the invention showing the motion action. As shown in FIG. 14 and FIG. 15, the motion device (13) is secured at an appropriate location on the base (1). The motion crank (131) of the motion device (13) is connected to the second drive device (14) by the motion shaft (132). Therefore, as shown in FIG. 14, when the motion device (13) starts to move in one direction, the motion crank (131) will, with respect to the motion shaft (132), bring the second drive device (14) making the pelvic part section (2), with respect to the first pivotally-connected shaft (112), follow the motion crank (131) of the motion device (13) to perform consecutive motion in the same motion direction. Therefore, the pelvic part section (2) will rotate in the first direction (a) to move in upward direction. Consequently, as shown in FIG. 15, if the motion device (13) continues to move in the same swinging direction, the pelvic part section (2) will rotate in the second direction (b) to move in downward direction. In this way, since the pelvic part section (2) is capable of swinging up-and-down, the continuing up-and-down swinging is capable of producing the function of a dynamic curvilinear lumber vertebrae traction motion.

Moreover, the adjusting rod (41) furnished by the leg part seat (43) of the leg part section (4) is capable of adjusting the length of the outer sliding rod (42) inserted within the outer sliding rod bearing tube (221) in accordance with the length of the leg of the user. As shown in FIG. 2, the ankle supporting rod (44) is secured at the center of the leg part seat (43) by the use of the supporting rod securing part (431). The center location of the ankle securing brace (45) is secured to the ankle supporting rod (44). The user is capable of employing the adjusting part (451) to adjust the height of the ankle securing brace (45) in accordance with the tightness of the ankle supports (46) pressing on the ankle of the legs.

Furthermore, as shown in FIG. 2, FIG. 14 and FIG. 15, the adjusting rod (61) of the cervical part traction section (6) is capable of adjusting the distance in accordance with the length of the arm of the user. The second supporting rod (63) is secured at the center of the handle rod (62) by the use of the supporting rod securing part (621). The adjusting seat (631) on the supporting rod (63) secured to the traction rod (64) can be used to adjust the height of the traction rod (64) by simultaneously adjusting the upper adjusting seat securing part (632) and lower adjusting seat securing part (633).

In conclusion, the chiropractic machine of the invention is capable of helping the user to perform rehabilitation, redress, traction for cervical vertebrae, and dynamic lumbar vertebrae traction etc. to improve the syndromes of cervical vertebrae bending, thoracic vertebrae bending, vertebral errors, adhesion, and prominent cartilage etc., thereby, to achieve the efficacies of soothing and treating the lower back pain and lower back paralysis.

It will become apparent to those people skilled in the art that various modifications and variations can be made to the structure of the invention without departing from the scope or spirit of the invention. In view of the foregoing description, it is intended that all the modifications and variation fall within the scope of the following appended claims and their equivalents.

What is claimed is:

1. A chiropractic machine, comprising:

A pelvic part section, comprising:
- a pelvic part seat;
- an outer sliding rod furnished on each lateral side of the pelvic part seat such that the outer sliding rods are parallel and that each outer sliding rod has two ends;
- an outer sliding rod sleeve tube;
- a central sliding rod;
- an adjusting rod inserted through a penetrating hole provided at the pelvic part seat, said pelvic part seat having a center section;
- a sliding bracing frame provided in the center section of the pelvic part seat;

a base, comprising:
- an elevating post having a first drive device;
- a motion device; and
- a second drive device comprising two ends with an end connected to the motion device and the other end connected to the pelvic part section;
- a third drive device connected to the pelvic part seat;
- a rotating handle furnished at the third drive device;
- a fourth drive device comprising two ends with one end connected to the sliding bracing frame which is positioned above the pelvic part seat, wherein the sliding bracing frame is connected to the outer sliding rod;

an abdominal part section, comprising:
- a bracing seat;
- an abdominal part seat having a tightening band buckle peg provided on each side of the abdominal part seat;
- a slide-down rod provided below the abdominal part seat;
- a second pivotally-connected shaft mounted on the bracing seat; and
- a fifth drive device comprising two ends having an end connected to the elevating post and the other end connected to the bracing seat;

a leg part section, comprising:
- an adjusting rod penetrating through the penetrating hole in the pelvic part seat, wherein the adjusting rod is parallel to the central sliding rod;
- a leg part seat furnished on the end of the outer sliding rod;
- an ankle supporting rod secured to the leg part seat by a supporting rod securing part;
- an ankle securing brace secured at the ankle supporting rod with an adjusting part provided to the ankle securing brace; and
- a pair of ankle supports attached on the ankle securing brace;

a head part section; comprising:
- a head pillow rack;
- a first supporting rod;
- a sixth drive device; and
- a handle seat;

a cervical part traction section, comprising:
- an adjusting rod;
- a handle rod connected to the adjusting rod;
- a second supporting rod having an adjusting seat thereon, wherein the second supporting rod is attached to the handle rod;
- a traction rod, wherein a center part of the traction rod is attached to the second supporting rod;
- a seventh drive device attached to the traction rod;
- a cervical part traction band secured to the traction rod; and a plurality of mattresses, wherein each mattress of the plurality of mattresses has a tightening band.

2. The chiropractic machine as claimed in claim 1, wherein a drive device is furnished in the motion device of the base.

3. The chiropractic machine as claimed in claim 1, wherein any of the first drive device, the second drive device, the third drive device, the fourth drive device, the fifth drive device, the sixth drive device, and the seventh drive device are driven by a motor.

4. The chiropractic machine as claimed in claim 1, wherein any of the first drive device, the second drive device, the third drive device, the fourth drive device, the fifth drive device, the sixth drive device, and the seventh drive device are driven by a hydraulic cylinder.

5. The chiropractic machine as claimed in claim 1, wherein any of the first drive device, the second drive device, the third drive device, the fourth drive device, the fifth drive device, the sixth drive device, and the seventh drive device are driven by a pneumatic cylinder.

6. The chiropractic machine as claimed in claim 1, wherein an adjusting part is furnished at the center of the ankle securing brace in accordance with requirements of the user.

7. The chiropractic machine as claimed in claim 1, further comprising a lower adjusting seat securing part.

8. The chiropractic machine as claimed in claim 1, wherein the plurality of mattresses comprises a plurality of tightening bands.

* * * * *